(12) United States Patent
Wales et al.

(10) Patent No.: US 12,213,657 B2
(45) Date of Patent: Feb. 4, 2025

(54) DEVICES AND METHODS FOR TISSUE RETRACTION

(71) Applicant: Boston Scientific Scimed, Inc., Maple Grove, MN (US)

(72) Inventors: Ryan V. Wales, Northborough, MA (US); Ramon Estevez, Lowell, MA (US); Nicholas J. Mazzola, Hudson, MA (US); Beth Benesh, Marlborough, MA (US); Nelly Nganga, Lowell, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1343 days.

(21) Appl. No.: 16/148,880

(22) Filed: Oct. 1, 2018

(65) Prior Publication Data

US 2019/0099172 A1 Apr. 4, 2019

Related U.S. Application Data

(60) Provisional application No. 62/566,596, filed on Oct. 2, 2017.

(51) Int. Cl.
| | | |
|---|---|---|
| *A61B 17/02* | (2006.01) | |
| *A61B 1/018* | (2006.01) | |
| *A61B 17/08* | (2006.01) | |
| *A61B 17/29* | (2006.01) | |
| *A61B 17/00* | (2006.01) | |

(Continued)

(52) U.S. Cl.
CPC .......... *A61B 17/0218* (2013.01); *A61B 1/018* (2013.01); *A61B 17/083* (2013.01); *A61B 17/29* (2013.01); *A61B 2017/00269* (2013.01); *A61B 2017/00296* (2013.01); *A61B 2017/0034* (2013.01); *A61B 2017/00862* (2013.01); *A61B 2017/0287* (2013.01); *A61B 17/10* (2013.01);

(Continued)

(58) Field of Classification Search
CPC ... A61B 17/0218; A61B 17/083; A61B 17/29; A61B 17/10; A61B 1/018; A61B 90/92; A61B 2017/00269; A61B 2017/00296; A61B 2017/0034; A61B 2017/00862; A61B 2017/0287; A61B 2090/037
See application file for complete search history.

(56) References Cited

U.S. PATENT DOCUMENTS

| | | |
|---|---|---|
| 8,038,612 B2 | 10/2011 | Paz |
| 8,397,335 B2 | 3/2013 | Gordin et al. |

(Continued)

FOREIGN PATENT DOCUMENTS

| | | |
|---|---|---|
| JP | 2005103107 A | 4/2005 |
| JP | 2006517831 A | 8/2006 |

(Continued)

OTHER PUBLICATIONS

International Search Report and Written Opinion for application No. PCT/US2018/053800, mailed on Mar. 19, 2019, 17 pages.

(Continued)

*Primary Examiner* — Anh T Dang
(74) *Attorney, Agent, or Firm* — Seager, Tufte & Wickhem, LLP (57) ABSTRACT

The present disclosure pertains to medical devices. More particularly, the present disclosure pertains to tissue retraction devices and related delivery systems and methods.

19 Claims, 9 Drawing Sheets

(51) Int. Cl.
  *A61B 17/10* (2006.01)
  *A61B 90/00* (2016.01)
  *A61B 90/92* (2016.01)
(52) U.S. Cl.
  CPC ......... *A61B 2090/037* (2016.02); *A61B 90/92* (2016.02)

(56) References Cited

U.S. PATENT DOCUMENTS

| | | | |
|---|---|---|---|
| 8,945,155 | B2 | 2/2015 | Gordin et al. |
| 9,463,003 | B2 | 10/2016 | Gordin et al. |
| 10,143,459 | B2 | 12/2018 | Heftman |
| 2003/0069592 | A1* | 4/2003 | Adams ............... A61B 17/1285 606/142 |
| 2004/0193185 | A1* | 9/2004 | McBrayer .......... A61B 17/1285 606/139 |
| 2005/0250987 | A1 | 11/2005 | Ewers et al. |
| 2010/0174150 | A1* | 7/2010 | Park ................... A61B 17/0218 600/218 |
| 2013/0211432 | A1 | 8/2013 | Terada |
| 2014/0235396 | A1 | 8/2014 | Baas et al. |
| 2014/0235936 | A1 | 8/2014 | Baas et al. |
| 2015/0272585 | A1 | 10/2015 | Park et al. |
| 2017/0215884 | A1 | 8/2017 | Satake et al. |
| 2020/0397445 | A1 | 12/2020 | Shikhman et al. |

FOREIGN PATENT DOCUMENTS

| | | |
|---|---|---|
| JP | 2007136128 A | 6/2007 |
| JP | 2009279333 A | 12/2009 |
| WO | 2013041960 A1 | 3/2013 |
| WO | 2019135958 A2 | 7/2019 |
| WO | 2019135958 A3 | 7/2019 |

OTHER PUBLICATIONS

Sakamoto, N., et al., "Endoscopic submucosal dissection of large colorectal tumors by using a novel spring-action S-O clip for traction (with video)", Gastrointestinal Endoscopy 69(7):1370-1374 (2009).

Fujii, T., et al., "A novel endoscopic suturing technique using a specially designed so-called "8-ring" in combination with resolution clips (with videos)", Gastrointestinal Endoscopy 66(6):1215-1220 (2007).

Matsumoto, K., et al., "T1594: A New Traction Device for Gastric Endoscopic Submucosal Dissecton (ESD): Two-Point Fixed by Latex Traction for Early Gastric Cancer", Gastrointestinal Endoscopy, 71(5):AB317 (2010).

Imaeda, H., et al., "Advanced endoscopic submucosal dissection with traction", World Journal of Gastrointestinal Endoscopy 6(7):286-295 (2014).

Sakamoto, N., et al.,"'Loop Clip' a new closure device for large mucosal defects after EMR and ESD", Endoscopy 40: E97-E98 (2008).

Fujihara, S., et al., "Management of a large mucosal defect after duodenal endoscopic resection", World Journal of Gastroenterology, 22(29):6595-6609 (2016).

Mori, H., et al., "The Loop Clip is Useful for Closing Large Mucosal Defects After Colorectal Endoscopic Submucosal Dissection: A Preliminary Clinical Study", Digestive Endoscopy 23:330-331 (2011).

Tsuji, K., et al., "Recent traction methods for endoscopic submucosal dissection", World Journal of Gastroenterology, 22(26):5917-5926 (2016).

Ritsuno, H., et al., "Prospective clinical trial of traction device-assisted endoscopic submucosal dissection of large superficial colorectal tumors using the S-O clip", Surgical Endoscopy 28:3143-3149 (2014).

Sakamoto, N., et al., "The facilitation of a new traction device (S-O clip) assisting endoscopic submucosal dissection for superficial colorectal neoplasms", Endoscopy, 40:E94-E95 (2008).

Takeda, T., et al., "Traction device to remove an adenoma in the appendiceal orifice by endoscopic submucosal dissection", Endoscopy 45:E239-E240 (2013).

Kato, M., et al., "Technical feasibility of line-assisted complete closure technique for large mucosal defects after colorectal endoscopic submucosal dissection", Endoscopy International Open, 5(1):E11-E16 (2017) DOI: http://dx.doi.org/10.1055/s-0042-121002.

International Preliminary Report on Patentability for the International Patent Application No. PCT/US2018/053800, mailed Apr. 16, 2020, 10 pages.

\* cited by examiner

DEVICES AND METHODS FOR TISSUE RETRACTION

PRIORITY

This application claims the benefit of priority under 35 USC § 119 to U.S. Provisional Patent Application Ser. No. 62/566,596, filed Oct. 2, 2017, which is incorporated by reference herein in its entirety and for all purposes.

FIELD

The present disclosure pertains to medical devices. More particularly, the present disclosure pertains to tissue retraction devices and related delivery systems and methods.

BACKGROUND

Endoscopic submucosal dissection is one of the largest growing forms of endoluminal surgery. Physicians use devices to provide a means of tissue traction. However, devices such as endoscopic caps may require large amounts of saline solution to continuously be injected into the lesion. Such procedures may include multiple device exchanges and extended procedure times. Often when traction is provided by an endoscopic cap, the physician may lose their bearings in relation to the target tissue margins. Alternative tissue traction devices are first delivered to the target tissue site and then require a tool such as a grasper to retrieve the device before engaging the target tissue. This process can be time consuming and complicated. In another example, the actual tissue that the physician is attempting to dissect may, itself, obstruct the pathway of the tools which the physician is using during the procedure. Therefore, in some instances it may be desirable to utilize a medical device which assists in improving the visualization of the target tissue while also mitigating the obstruction of dissection tools the physician is utilizing. It may be further desirable to utilize a tissue retraction device that is able to be positioned and controlled to efficiently engage, lift and retract the region of target tissue to be dissected by the physician.

It is with these considerations in mind that the improvements of the present disclosure may be advantageous.

SUMMARY

The present disclosure, in its various aspects, is directed generally to medical devices, and more specifically to tissue retraction devices, methods, and related delivery systems. Embodiments of tissue retraction devices, methods, and related delivery systems according to the present disclosure, including as described herein, may decrease complications around tissue retraction procedures, such as visualization, procedure time, and procedure complexity.

Various embodiments of the present disclosure may include a tissue retraction device with a cap having a proximal end, a distal end, and a lumen therethrough. An extension member may extend distally from the distal end of the cap. The extension member may be configured to engage a first engagement member such that the first engagement member is positioned at an angle with respect to a longitudinal axis of the cap lumen. The proximal end of the cap may be configured for mounting onto a distal end of an endoscope. The angle with respect to a longitudinal axis of the cap lumen may be about 90 degrees. The extension member may engage a spring of the first engagement member such that the spring is disposed about the extension member. A clip may be disposed on the cap. The clip may be configured to engage a second engagement member. The clip may be configured to grasp a spring of the second engagement member. The clip may be configured to orient the second engagement member substantially parallel to the longitudinal axis of the cap lumen. The clip may be disposed on an inner surface of the cap lumen. The first engagement member may be oriented normal to the second engagement member when engaged on the cap. An elastic member having a distal end, proximal end and length therebetween may be connected at the distal and proximal ends to the respective first and second engagement members. The elastic member may be connected to a spring of the first engagement member. The elastic member may be connected to a spring of the second engagement member.

Various embodiments of the present disclosure may include a tissue retraction system comprising a cap having a proximal end, a distal end, and a lumen therethrough. An extension member may extend distally from the distal end of the cap. The system may include a first engagement member. The extension member may be configured to engage the first engagement member such that the first engagement member is positioned at an angle with respect to a longitudinal axis of the cap lumen. The system may include a second engagement member. The angle with respect to a longitudinal axis of the cap lumen may be about 90 degrees. The second engagement member may be oriented substantially parallel with the longitudinal axis of the cap lumen. A clip may be disposed on the cap that is configured to engage the second engagement member.

Various embodiments of the present disclosure may include a method of retracting tissue including a grasping member inserted distally through a working channel of a device and cap that is oriented at a distal end of the device. A first engagement member may be disengaged from a mounted position in the cap with the grasping member. The first engagement member may be connected by a tether to a second engagement member in a mounted position in the cap. The first engagement member may be removed from the mounted position. The grasping member may be translated distally. The second engagement member may be removed from the mounted position by the tether pulling on the second engagement member.

Various embodiments of the present disclosure may include a tissue retraction system comprising a first engagement member having a first end configured to engage tissue. A pair of gripping members may be proximal to the first end. A grasping member with a pair of arms may be configured to grasp the first engagement member. Each one of the pair of arms may be configured to interface with a respective one of the pair of gripping members. The pair of gripping members may each have a substantially convex surface. The convex surface of one of the pair of gripping members may be facing away from the other one of the pair of gripping members. The pair of arms may each have a substantially concave surface. The concave surface of one of the pair of arms may face towards the other one of the pair of arms. Each arm of the pair of arms may substantially surround a corresponding gripping member of the pair of gripping members. The pair of arms may each have a distal portion that extends past the corresponding gripping member in a distal direction and bends towards the opposing arm. The pair of arms may each have a finger that extends perpendicular to a longitudinal axis of each arm. The pair of gripping members may be proximal to the fingers. The arms and fingers of the grasping members together may define a pocket around the pair of gripping members. The grasping member may be configured to actuate and compress the pair of gripping members towards each other. A longitudinal axis of the first engagement member may be substantially parallel to a longitudinal axis of the arms. A destructible member may be connected between the pair of gripping members. A tether having a loop at a distal end may be connected to the destructible member. The destructible member may separate when the gripping members are compressed towards each other. The system may further comprise a pair of springs. Each spring may be connected to the grasping member and facing in a direction substantially towards the gripping members. The surface of one gripping member may face in a direction substantially away from the other gripping member. The system may further comprise a catheter. The catheter may include a distal end having a diameter narrower than a diameter of the rest of the catheter. The system may further comprise a first working channel of a device having a lumen. The grasping member may engage the pair of gripping members and may be contained within the working channel. The first working channel may be in an endoscope. The system may further comprise a second working channel of the device. The second working channel may be independent to, external to, and/or in an endoscope. If independent or external to the endoscope, the second working channel may have a distal end face that is substantially normal to a distal end face of the first working channel. A second engagement member may be loaded into the second working channel. The second engagement member may be tethered to the first engagement member. The system may further comprise a casing having a first open end, a second closed end, and a body therebetween disposed about the first end of the first engagement member. The casing may be linearly perforated from the first end at least substantially up to the second end. The body may include a first piece extending from the first open end to the second closed end. A second piece may extend from the first open end to the second closed end. The first engagement member may be tethered to a rotatable grasping clip.

Various embodiments of the present disclosure may include a method of retracting tissue including back-loading a first working channel of an endoscope with a first grasping member extending out a distal end of the endoscope. A second working channel of the endoscope may be back-loaded with a second grasping member extending out the distal end of the endoscope. A first engagement member may be loaded having a first end configured to engage tissue and a second end, such that the first grasping member may be disposed about the first end of the first engagement member. A second engagement member may be loaded having a first end configured to engage tissue and a second end, such that the second grasping member may be disposed about the first end of the second engagement member. The first and second grasping members and first and second engagement members may be encapsulated in a cylindrical cap extending from the distal end of the endoscope. The first end of the first and second engagement members may be oriented in a distal direction that is substantially parallel to a longitudinal axis of the endoscope.

In various embodiments of the present disclosure, a medical professional may manipulate a distal end (e.g., first end) of an engagement member toward a target tissue. A grasping member may acquire an engagement member by manipulating the arms of the grasping member around one or more of the gripping members of the engagement member. For example, the grasping member may open and then close its arms around the gripping members of an engagement member, opening the first end of the engagement member for engaging tissue. The grasping jaws may manipulate the location of the engagement member such that the first end of the engagement member is adjacent the target tissue. The grasping member may be actuated to open its arms thereby releasing the engagement member and allowing the first end of the engagement member to engage the target tissue. A second engagement member may be similarly manipulated by the grasping member. The second engagement member may be attached to the first engagement member (e.g., by an elastic member). The second engagement member may be engaged to another section of the target tissue, or to healthy tissue, so as to anchor the device and target tissue while a medical professional dissects the target tissue. Should both the first and second engagement members be attached to the target tissue to be dissected, the elastic member may place the target tissue under tension. Once the target tissue is dissected, the elastic member may pull the engagement members towards each other, retracting the target tissue away from the wall of the body lumen.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Various embodiments according to the present disclosure are described below. As used herein, "proximal end" refers to the end of a device that lies closest to the medical professional, and "distal end" refers to the end of an implanted or positioned device or object that lies furthest from the medical professional.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, including intravascular procedures, procedures along the digestive and/or biliary tract, thoracic procedures, etc. utilize medical devices to access tissue intended for removal (e.g., "target tissue") within the body. For example, in some current medical procedures (e.g., Endoscopic Submucosal Dissection (ESD), Peroral Endoscopic Myotomy (POEM), cholecystectomy, Video-Assisted Thoracoscopic Surgery (VATS)), physicians may utilize an endoscope or similar medical device to access and remove cancerous lesions. Further, as part of the procedure, the physician may utilize an endoscope capable of both accessing the target tissue site while also permitting a cutting device to be deployed therethrough to retract the target tissue. Additionally, in some instances, the endoscope may incorporate features which assist the physician in visualizing and performing the tissue dissection procedure. For example, some endoscopes may include a light and/or camera designed to illuminate the body lumen as the endoscope is navigated and positioned adjacent to the target tissue site. Additionally, some endoscopes may also include a lumen (e.g., a working channel) through which a cutting member, grasping member, or other accessory medical devices may be deployed and utilized.

While physicians are becoming more proficient at retracting cancerous lesions from within the body (e.g., within the digestive tract, abdominal cavity, thoracic cavity, etc.), the retraction methods continue to be inefficient and time-consuming. For example, in some instances poor visualization of the tissue dissection process may result in a prolonged tissue dissection procedure. In another example, the actual tissue that the physician is attempting to dissect may, itself, obstruct the pathway of the tools which the physician is using during the procedure. Therefore, in some instances it may be desirable to utilize a medical device which assists in improving the visualization of the target tissue while also mitigating the obstruction of dissection tools the physician is utilizing. It may be further desirable to utilize a tissue retraction device that lifts and retracts the region of target tissue to be dissected by the physician.

Disclosed herein are medical devices such as tissue retraction devices and delivery systems that are designed to efficiently engage, lift, and/or retract the target tissue. Some other example devices which may complement devices and methods of the present disclosure are disclosed in U.S. Provisional Application No. 62/473,957, which is incorporated in its entirety and for all purposes.

Figure 1:
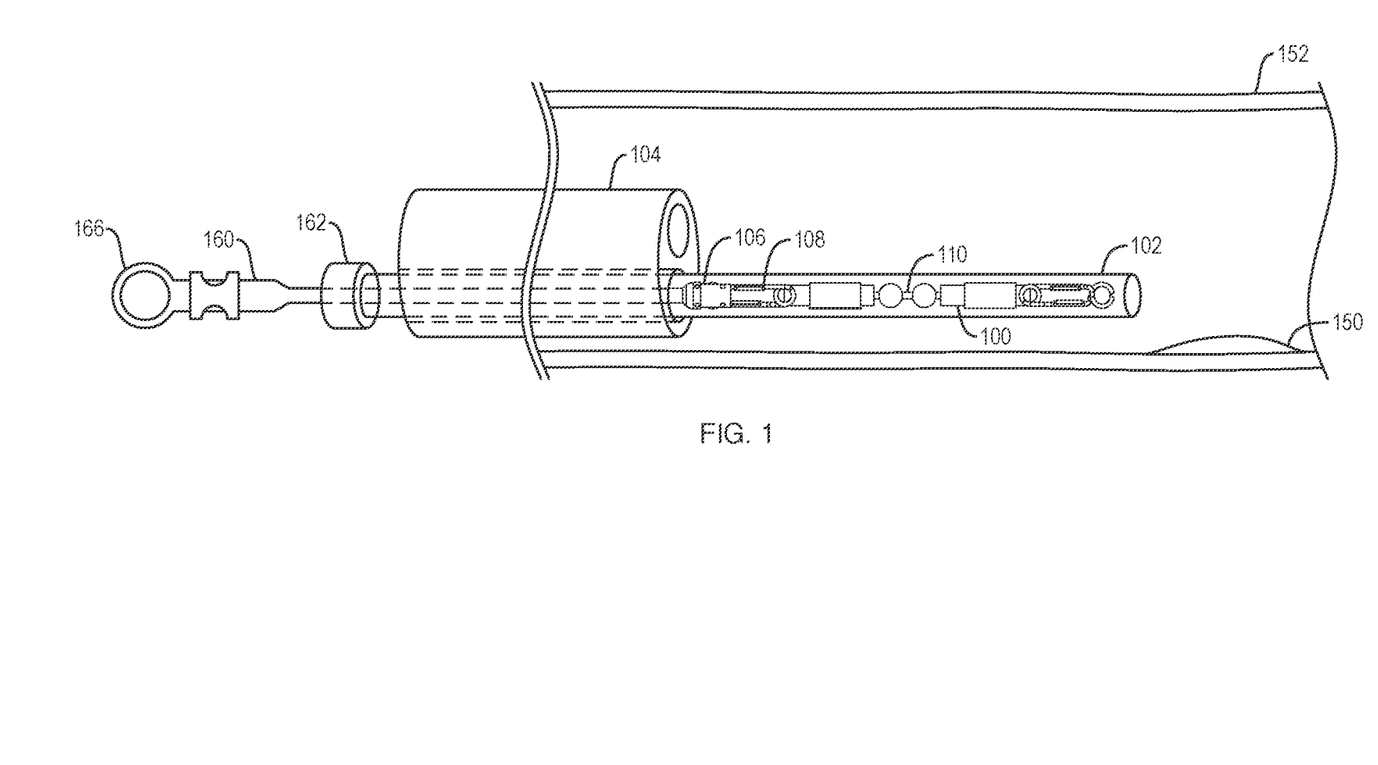
FIG. 1 depicts a tissue retraction system within a body lumen in accordance with an embodiment of the present disclosure.

Referring to FIG. 1, various embodiments of a tissue retractor system may include a tissue retraction device 100 loaded into a delivery catheter 102 that may also be within a working channel of an endoscope 104. The working channel may be a lumen of a medical device. The working channel may permit a variety of medical devices to pass therethrough. A medical professional may pass or exchange a variety of medical devices through the working channel over the course of a given medical procedure. For example, as illustrated in FIG. 1, the catheter 102 may extend through the working channel whereby a distal end of the catheter 102 may eventually extend out of the working channel to a position adjacent the target tissue 150. The working channel may take the form of a working channel of an endoscope, such as endoscope 104 or a laparoscope, or the lumen of a needle, catheter, guide tube, or the like. The system may include a grasping member 106 that is proximal to and/or grasping an engagement member 108 within the catheter 102. An elastic member 110 may connect one or more engagement members 108. The system is directed towards a target tissue 150 for retraction of target tissue 150 within a body lumen 152. A proximal portion 160 of the tissue retraction system may extend out of the body lumen 152. In some embodiments, the grasping member 106 may advance (e.g., push, deploy, etc.) the tissue retraction device 100 out of the distal end of the catheter 102. When positioned within the catheter 102 the grasping member 106 may be in a closed position (e.g., the arms or jaws of the grasping member 106 may be closed and contacting one another and/or may grasp the device 100).

The grasping member 106 may deploy the tissue retraction device 100 out of catheter 102. With the tissue retraction system positioned in proximity to the target tissue 150, a medical professional may advance the grasping member 106 distally within the catheter 102 such that the grasping member 106 may contact the proximal end of the tissue retraction device 100, and push it out of the catheter 102. A handle 166 may control the opening and/or closing of the grasping member 106. When the grasping member 106 is advanced distally outside of the catheter 102, a medical professional may manipulate the handle 166 to open and/or close the grasping member 106. Once the grasping member 106 has pushed the tissue retraction device 100 out of the catheter 102, the grasping member 106 may be used to position and/or manipulate the tissue retraction device 100 within the body lumen 152.

In some embodiments, the grasping member 106 and the tissue retraction device 100 may be positioned within a catheter 102 as depicted in FIG. 1 prior to the catheter 102 being advanced through the working channel of an endoscope 104. In some embodiments, both the grasping member 106 and the tissue retraction device 100 may be preloaded into the catheter 102 prior to being inserted and advanced through the working channel of the endoscope 104. In other examples, however, only the tissue retraction device 100 may be preloaded into the catheter 102 and advanced within the working channel of the endoscope 104 and the grasping member 106 may be separately inserted into the catheter 102 and advanced distally to a position in which grasping member 106 is adjacent, contacting, and/or grasping the proximal end of the tissue retraction device 100. In further examples, the tissue retraction device may be advanced down a working channel of an endoscope or other lumen without catheter 102.

It can be appreciated that various embodiments of a tissue retraction system, described here or otherwise, within the scope of the present disclosure, may be designed such that the catheter 102 and the grasping member 106 may be moved (e.g., translated, rotated, etc.) relative to one another. For example, once the distal end of the catheter 102 is positioned adjacent to the target tissue 150 (with the grasping member 106 positioned adjacent to the tissue retraction device 100), a medical professional may grasp both control member 162 and the handle member 166 (e.g., with a thumb through handle 166 and fingers engaging the distal surface of control member 162). This may permit the medical professional to maintain the position of the catheter 102 while advancing the grasping member 106 in a distal direction such that the grasping member 106 moves distally relative to the catheter 102. It can be appreciated that this relative movement may push the tissue retraction device 100 out of the distal end of the catheter 102. In other examples, it can be appreciated that instead of a medical professional advancing the grasping member 106 in a distal direction to deploy the tissue retraction device 100, the medical professional may alternatively or additionally retract the delivery catheter 102 proximally while maintaining the grasping member 106 in a fixed position. The proximal retraction of the catheter 102 may deploy the tissue retraction device 100, thereby releasing it from the catheter 102.

Figure 2:
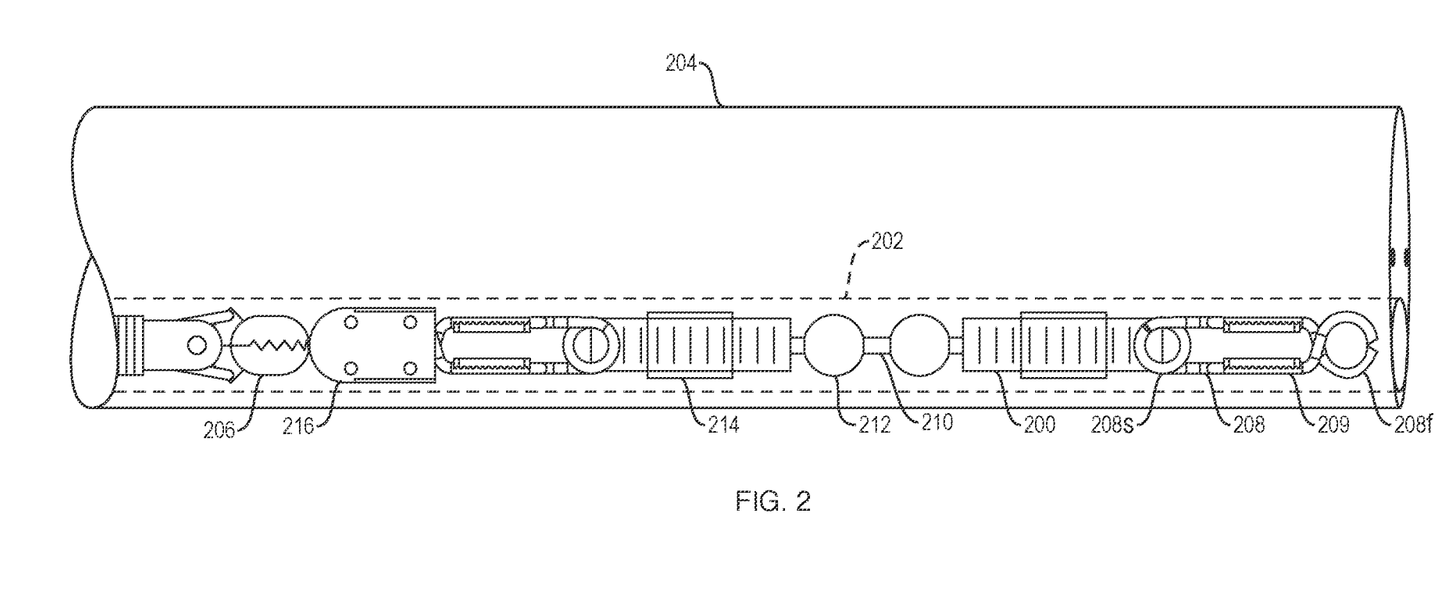
FIG. 2 depicts a side view of a tissue retraction system in accordance with an embodiment of the present disclosure.

Referring to FIG. 2, various embodiments of a tissue retractor system may include an endoscope 204 having a working channel 202. A tissue retraction device 200 may be loaded within the working channel 202. Alternatively, a catheter (not depicted) may also be included within the working channel 202, or a catheter may replace the endoscope 204. The device 200 includes a first engagement member 208 having a first end 208f configured to engage tissue (e.g., arms or jaws) and a second end 208s that may be a spring. A pair of gripping members 209 are disposed on the engagement member 208 between the first end 208f and the second end 208s (e.g., proximal to the first end 208f). An elastic member 210 connects the second end 208s of the first engagement member 208 to the second end 208s of the second engagement member 208. An alignment member 214 about the elastic member 210 may increase the rigidity of the elastic member 210. The elastic member includes one or more swivels 212 that allow each portion of the elastic member 210 on one side of the swivel 212 to rotate independent of each portion of the elastic member on the other side of the swivel 212. A casing 216 may cover the first end 208f of the second (proximal) engagement member 208. The casing 216 has a first open end, a second closed end, and a body therebetween. The casing 216 separates and protects the first end 208f of the engagement member 208 configured to engage tissue from contacting the working channel 202. A grasping member 206 with a pair of arms is proximal to and pushing against the engagement member 208 and the casing 216.

In some embodiments, after a tissue retraction device 200 has been deployed out, e.g., out of the distal end of working channel 202 of endoscope 204 or catheter 102, the grasping member 206 may be utilized to position and/or attach the tissue retraction device 200 to the target tissue 150 within a body lumen 152. It can be appreciated that the gripping members 209 may be designed to be engaged by the grasping member 206. The gripping members 209 may provide an interface for the grasping member 206 to engage, attach, grip, grab, capture, etc. Further, the gripping members 209 may be designed such that they permit the grasping member 206 to efficiently acquire, position (and/or reposition), and open/close the first end 208f (e.g., jaws or arms) of the engagement members 208 by compressing the pair of gripping members 209 of an engagement member 208 towards each other. The gripping members 209 may have a surface that conforms with an arm of the grasping member 206. For example, the gripping members 209 may have a curved and/or textured surface to ensure adequate interface with an arm of the grasping member 206. While FIG. 2 depicts the gripping members 209 located between the first end 208f and the second end 208s of the engagement members 208, it is contemplated that gripping members may be located along other portions of engagement members. For example, depending on the configuration and location of the spring, the gripping members may be positioned on the first end and/or the second end of the engagement members.

An engagement member of the present disclosure may include a first end configured to engage tissue. The first end may be a pair of jaws that may be biased towards each other to pinch/grasp/hold tissue. A second end of the engagement member may be a spring that may hold the first end that is configured to engage tissue in a tissue engagement configuration (e.g., with the jaws of the first end closed). A pair of gripping members may be disposed between the first and second end of the engagement member. Compression of these gripping members may drive the first end to open by working against the spring coil at the second end. While embodiments for the engagement members of the present disclosure illustrate jaws at a first end for engaging tissue, a spring at a second end, and gripping members between the ends, other configurations are contemplated. For example, a "clothes-pin" configuration of compressed jaws at a first end, a pair of gripping pads at a second end, and a spring between the ends may be suitable.

An elastic member 210 of a tissue retraction device may tether a first engagement member 208 to a second engagement member 208. The elastic member 210 may be a band, rope, cord, leash, strap, strand, etc. The elastic member 210 may include a variety of cross-sectional geometries, e.g., circular, rectangular, triangular, or the like. The elastic member 210 may be bioabsorbable. The elastic member 210 may be coupled to the second end 208s of both the first engagement member 208 and the second engagement member 208. In one embodiment, the elastic member 210 may be attached to each engagement member 208 by compression forces between the coils of a spring on a second end 208s of the engagement members. In another embodiment, one or both ends of the elastic member 210 may be looped around one or more engagement members 208. An elastic member 210 may be connected to an engagement member 208 with a knot, an adhesive, a pin, and/or a snap. An elastic quality of the elastic member 210 may place the engagement members 208 in tension towards each other. This tension may allow the engagement members 208 that are connected by the elastic member 210 and that are engaged with target tissue 150 to pull/retract the target tissue 150 from the body lumen 152 and/or towards the opposing engagement member 208. One or more portions of the elastic member 210 may be brightly colored to allow a medical professional to more easily view the elastic member 210. Opposing ends of the elastic member 210 may vary in color to identify a specific end that may correspond to a particular engagement member 208. The colored elastic member 208 may also lighten in color as the pigment is stretched over a longer length, allowing a medical professional to identify a degree of elongation and relative amount of tension being applied by the engagement member on the tissue during a procedure. An elastic member 210 may or may not include one or more swivels 212. A swivel 212 may be positioned between and coupled to two segmented sections of the elastic member 210. Swivel 212 may be designed to permit the first engagement member 208 and a first segment of the elastic member 210 to rotate relative to the second engagement member 208 and a second segment of the elastic member 210 (e.g., rotating independently around a central axis of the tissue retraction device 200). A swivel 212 may be designed to provide complete rotation (e.g., 360-degree rotation) or to provide partial rotation (e.g., less than 360-degree rotation). It is contemplated that the swivel 212 may include alternative design arrangements, features, geometries, etc.

In various embodiments, a tissue retraction device may include one or more alignment members 214. An alignment member 214 may include a sabot, fairing, scaffolding, separator, housing, cover, shell, splitting tube, or the like. A device may include multiple alignment members 214 along the elastic member 210 (e.g., FIG. 2), a device may include one alignment member that covers more of the elastic member than that shown in FIG. 2, or a device may not have an alignment member. An alignment member may be a tubular member having a first end, a second end and a lumen extending therein. The lumen may extend from the first end to the second end. While FIG. 2 depicts the alignment members 214 as tubular members, other cross-sectional shapes of alignment members 214 are contemplated. For example, the cross-sectional shape of an alignment member 214 may be rectangular, triangular, ovular, square, or the like. One or more alignment members 214 may be disposed along the elastic member 210. For example, the elastic member 210 may extend through one or more alignment members 214. In some examples, one or more alignment members 214 may be long enough to prevent the elastic member 210 and/or an engagement member 208 from curling onto and/or entangling with itself or other components of the device 200 or endoscope 204.

Figure 3:
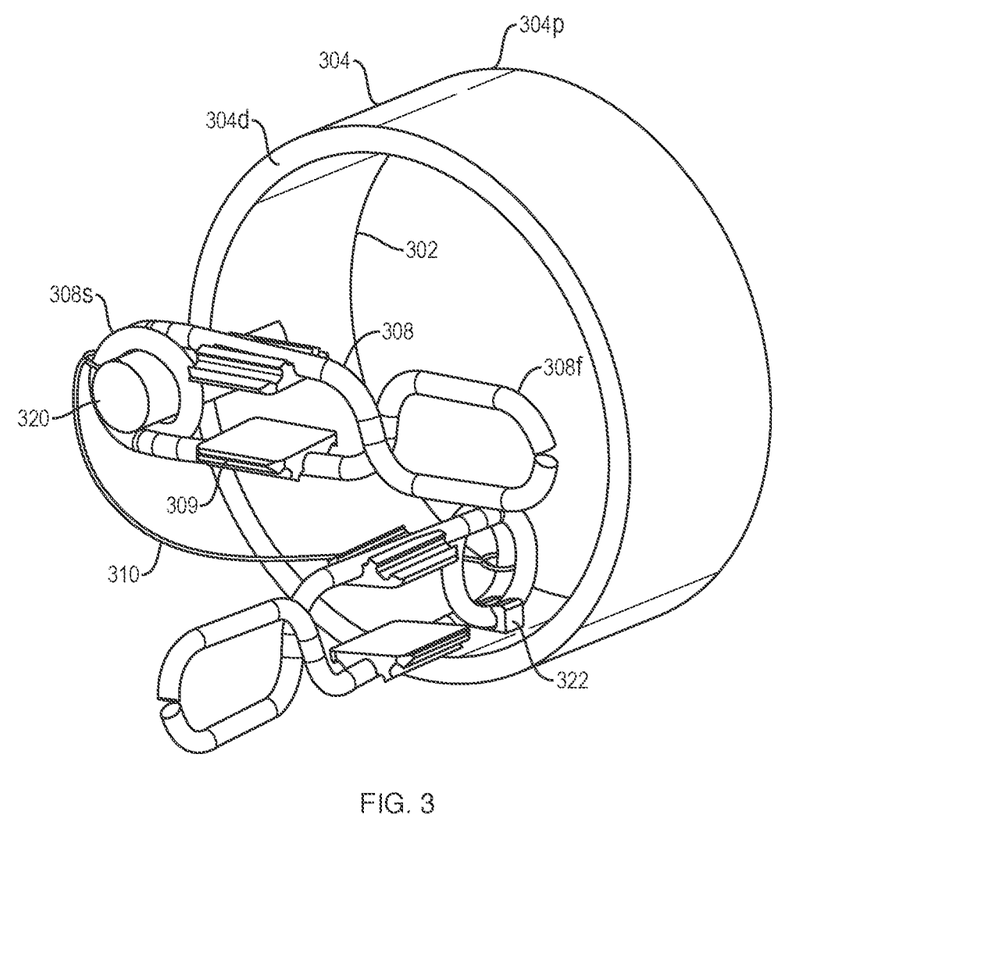
FIG. 3 is an isometric view of a tissue retraction device with a cap and engagement members in accordance with an embodiment of the present disclosure.

Referring to FIG. 3, various embodiments of a tissue retractor system, described here or otherwise, within the scope of the present disclosure, may include a cap 304 having a proximal end 304p, a distal end 304d, and a lumen 302 therethrough. The proximal end 304p is configured to mount on a distal end of an endoscope. The cap 304 has an extension member 320 disposed on the distal end 304d of the cap 304 that extends in the distal direction. The extension member 320 is configured to engage a first engagement member 308 in a mounted position. The extension member 320 engages the second end 308s such that a spring of the second end 308s surrounds the extension member 320. Extension member 320 is shown as a post in FIG. 3, which receives the spring of engagement member 308, but other configurations are contemplated. The first engagement member 308 is positioned at an angle with respect to a longitudinal axis of the lumen 302. The angle depicted in FIG. 3 is about 90 degrees, but other angles of orientation are contemplated such as 0 to 270 degrees, and any degree of angle in between. An angle of about 90 degrees orients the gripping members 309 perpendicularly to the longitudinal axis of the lumen 302. A grasping member may be translated distally out of the endoscope and into the lumen 302. The grasping member may grasp hold of the perpendicular gripping members 309 of the first engagement member 308. With the first engagement member 308 grasped by the grasping member, the grasping member may be translated distally further through the lumen 302 such that the second end 308s of the first engagement member 308 slides off of the extension member 320. The grasping member may then position the first engagement member 308 towards the target tissue within a body lumen. The cap 304 may include a clip 322, or other configuration of attachment device, that is configured to accept a second engagement member 308. The clip 322 may engage a spring at a second end 308s of the second engagement member 308. The clip 322 may be configured to orient the second engagement member 308 substantially parallel to the longitudinal axis of the lumen 302 in a mounted position. This orientation may be substantially normal/perpendicular to the first engagement member. The clip 233 may be disposed on an inner surface of the lumen 302. An elastic member 310 may connect the first and second engagement members 308. The elastic member 310 may be attached to a second end 308s of each of the first and second engagement members 308, which may be a spring. As the first engagement member 308 is removed away from the extension member 320, the elastic member 310 may pull the second engagement member 308 out of the clip 322. The grasping member may position the first engagement member 308 in target tissue with the second engagement member 308 attached via the elastic member 310.

Figure 4:
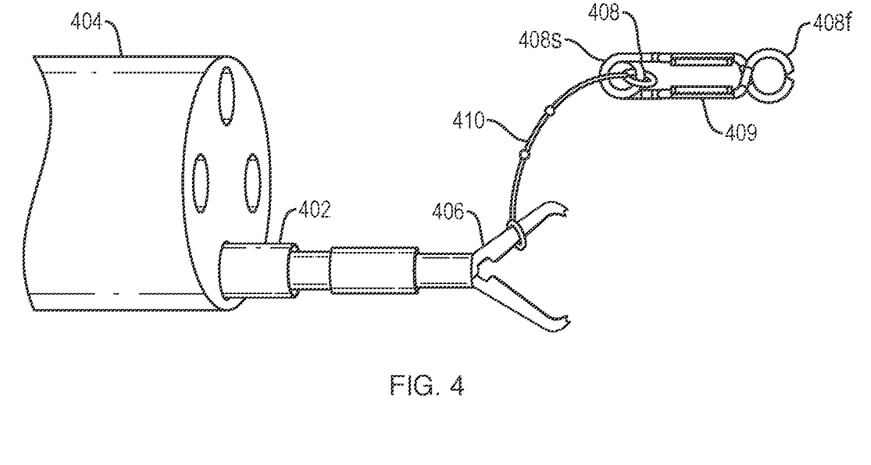
FIG. 4 depicts a tissue retraction system in accordance with an embodiment of the present disclosure.
Figure 5A:
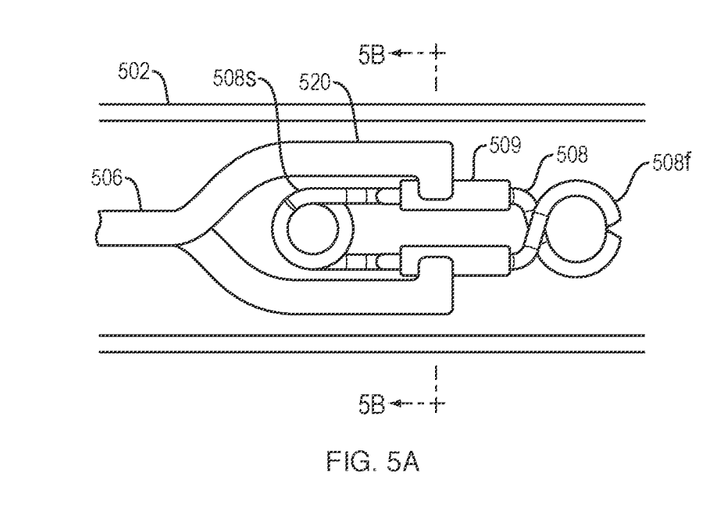
FIGS. 5A and 5B depict a tissue retraction system in accordance with an embodiment of the present disclosure.
Figure 5B:
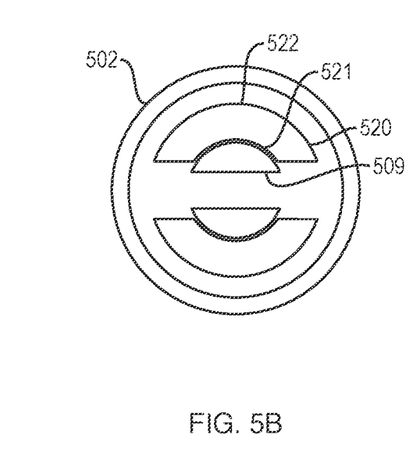

Referring to FIG. 4, various embodiments of a tissue retractor system, described here or otherwise, within the scope of the present disclosure, may include a grasping member 406 (e.g., a rotatable grasping clip, such as a RESOLUTION™ clip device sold by Boston Scientific Corporation, with a pair of jaws/arms, etc.). The grasping member 406 may be disposed within a catheter 402 and/or within a first working channel of an endoscope 404. An arm or jaw of the grasping member 406 may be attached to an end of an elastic member 410. Another end of the elastic member may be attached to a second end 408s of an engagement member 408. The grasping member 406, elastic member 410, and engagement member 408 may be loaded from the proximal or distal end of the endoscope 404 or catheter 402 into the catheter 402 and/or the working channel of the endoscope 404 or the grasping member may be loaded proximally and the engagement member 408 may be loaded from a distal end. The engagement member 408 may be loaded proximal, adjacent, or distal to the grasping member 406. The engagement member 408 may be pushed and/or pulled out of the catheter 402 by the elastic member 410 and/or grasping member 406. An additional tool (e.g., grasping member) may be introduced near the target tissue to grab the gripping members 409 and engage tissue with the first end 408f of the engagement member 408. The system may include a second working channel that may be independent of or external to the endoscope 404 or may be included in the endoscope 404. An independent second working channel of a device having a lumen may have a distal end face that is substantially normal to a distal end face of the first working channel. The independent second working channel of a device may be an independent endoscope, the same endoscope 404 as the first working channel, an additional catheter, or other tubular device. The engagement member 408 (and/or an additional engagement member that is tethered to the engagement member 408) may be loaded into the second working channel. When the grasping member 406 is delivered distally out of the first working channel, the one or more engagement members 408 may be pulled out of the second working channel. As the engagement member 408 is pulled out of the second working channel, it is angled at 90 degrees (i.e., perpendicular to the working channel, grasping member 406, or an additional grasping member) allowing for the arms of the grasping member 406 (or an additional grasping member) to easily interface with the gripping members 409.

Referring to FIGS. 5A-5B and 6A-6B, various embodiments of a tissue retractor system, described here or otherwise, within the scope of the present disclosure may include a grasping member 506 or 606 having a pair of arms 520 or 620. The grasping member 506 or 606 may be loaded into a catheter 502 or 602 and may be grasping an engagement member 508 or 608. Alternatively, the grasping member 506 or 606 may be loaded into the catheter 502 or 602 proximal to the engagement member 508 or 608. A longitudinal axis of the engagement member 508 or 608 (i.e., from the first end 508f or 608f to the second end 508s or 608s) may be substantially parallel to a longitudinal axis of one or more of the arms 520 or 620. Each arm 520 or 620 may be configured to interface with a respective one of the pair of gripping members 509 or 609. For example, each arm 509 or 609 may have a substantially concave surface 521 or 621 facing towards the other arm 520 or 620. The pair of arms 520 or 620 may each substantially surround at least one of the gripping members 509 or 609. The pair of gripping members 509 or 609 may each have a convex surface facing away from the other of the pair of gripping members 509 or 609. The convex surface of the gripping members may be configured to conform to and seat within the concave surfaces of the arms. The grasping member 506 or 606 may be configured to actuate and compress the pair of gripping members 509 or 609 towards each other.

Figure 6A:
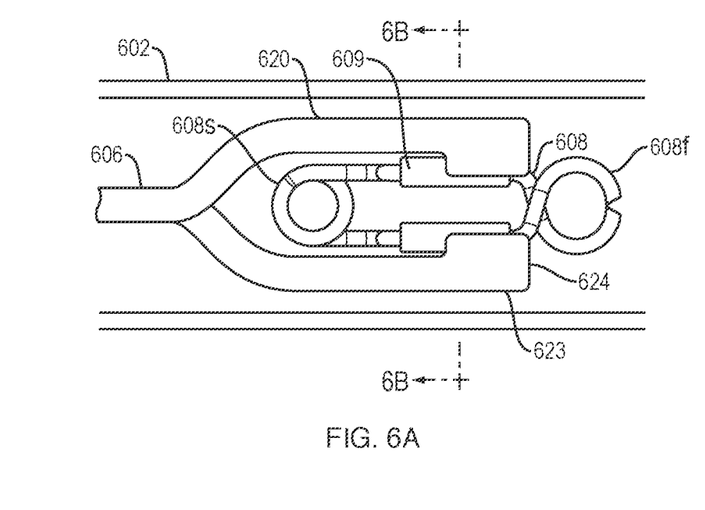
FIGS. 6A and 6B depict a tissue retraction system in accordance with an embodiment of the present disclosure.
Figure 6B:
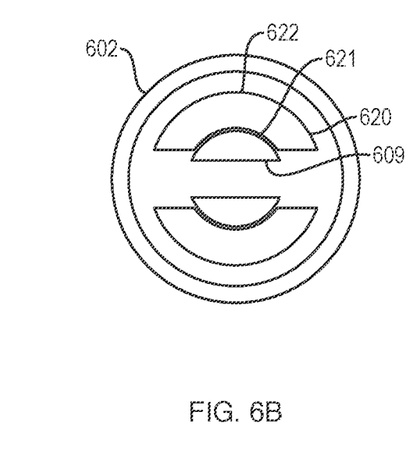

Referring to FIGS. 6A and 6B, a pair of arms 620 may each have a distal portion 623 that may extend past at least one of the gripping members 609 in a distal direction and also may bend towards the opposing arm 620. The pair of arms 620 may each have a finger 624 that extends perpendicular to a longitudinal axis of each arm 620. The pair of gripping members 609 may be proximal to the fingers 624 during delivery. The arms 620 and fingers 624 together may form around the pair of gripping members 609, defining a pocket within which the engagement member is secured against unwanted movement prior to being deployed.

Figure 7:
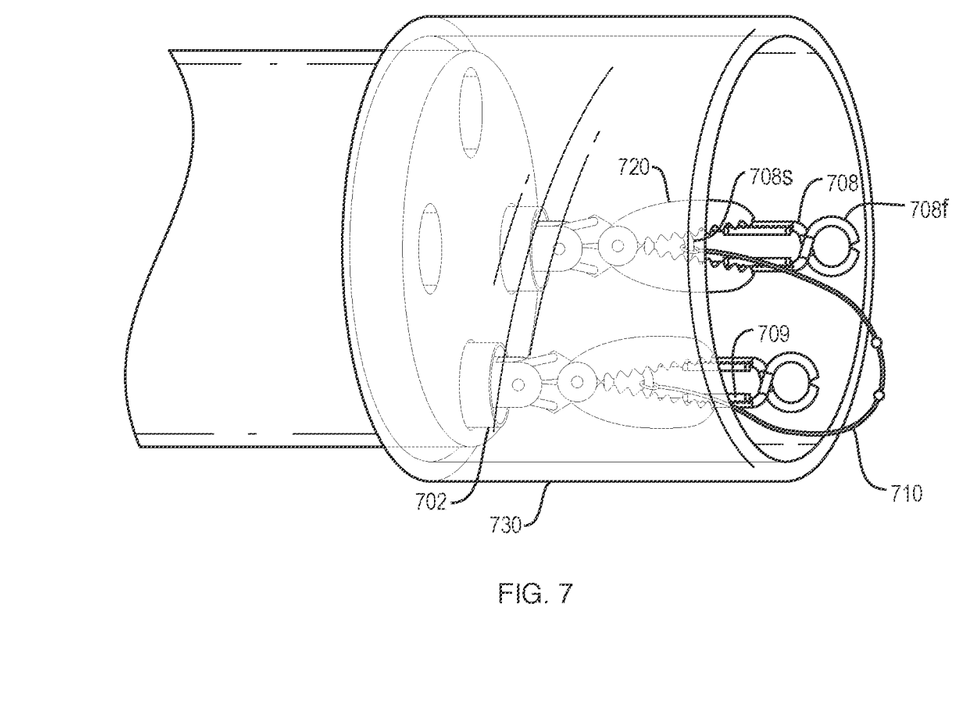
FIG. 7 depicts a tissue retraction system in accordance with an embodiment of the present disclosure.

Referring to FIG. 7, various embodiments of a tissue retractor system and method, described here or otherwise, within the scope of the present disclosure may include loading an endoscope 704 with two grasping members 706, alone and/or carried within catheters 702, into one or two working channels of the endoscope 704. The grasping members 706 may be front-loaded into the working channels (i.e., distally) or they may be back-loaded (i.e., proximally) into the working channels. The grasping members 706 of FIG. 7 are extending out of the distal end of the endoscope 704. Engagement members 708 may be loaded into the grasping members 706 such that the grasping members 706 are disposed about the engagement members 708. One or both engagement members 708 may be oriented in a distal direction that is substantially parallel to a longitudinal axis of the endoscope 704. One or both engagement members 708 may be oriented at an angle with respect to a longitudinal axis of the endoscope 704, for example, substantially transverse. A cylindrical cap 730 may be mounted to the distal end of the endoscope 704 and may extend in a distal direction that is substantially parallel to a longitudinal axis of the endoscope 704. The cap 730 may encapsulate the grasping members 706 and engagement members 708. The system shown in FIG. 7 may be assembled outside of the patient and then delivered inside a body lumen of the patient. The cap 730 may protect the body lumen of a patient against the assembly inside the cap 730 contacting the body lumen during insertion/delivery of the system. The cap 730 may have rounded edges in order to not scrape/scratch bodily tissue.

Figure 8A:
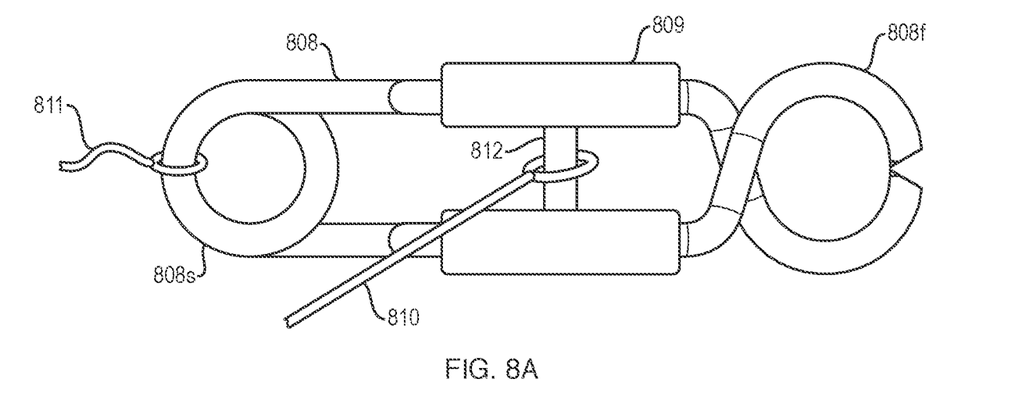
FIGS. 8A and 8B are a right view of a tissue retraction device in accordance with an embodiment of the present disclosure.
Figure 8B:
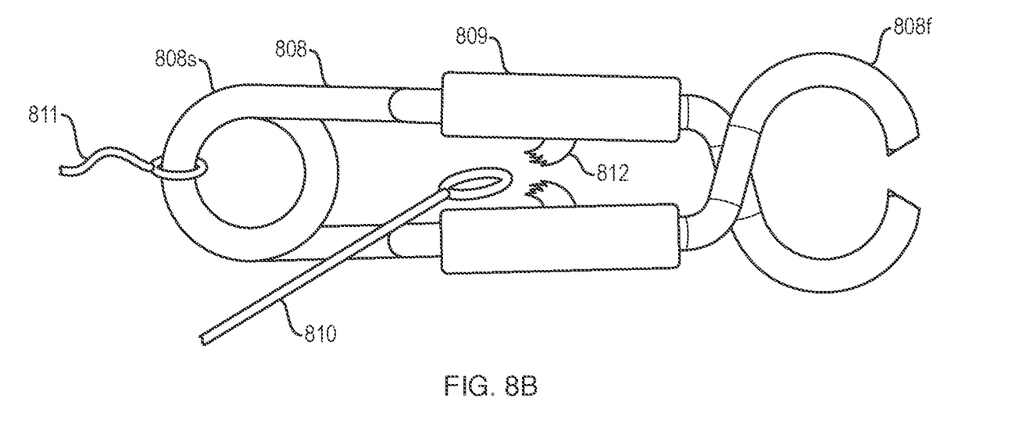

Referring to FIGS. 8A and 8B, various embodiments of a tissue retractor system, described here or otherwise, within the scope of the present disclosure, may include an engagement member 808 having a first end 808f configured to engage tissue (e.g., arms or jaws) and a second end 808s that may be a spring. A pair of gripping members 809 may be disposed on the engagement member 808 between the first end 808f and the second end 808s (e.g., proximal to the first end 8080. A destructible member 812 is connected between the pair of gripping members 809. A tether 810 having a loop at a distal end is connected to the destructible member 812. The engagement member 808 may be delivered into a body lumen with the tether 810 attached to the destructible member 812 such that the tether 810 extends proximally through the working channel and towards a working professional. The medical professional is able to keep track of and manipulate the engagement member 808 by manipulating the tether 810. The tether 810 may allow the medical professional to pull the engagement member 808 closer to a grasping member. At any point, the medical professional may compress the gripping members 809 towards each other (e.g., with a grasping member). When the gripping members 809 are compressed towards each other, the destructible member 812 may fracture (e.g., as shown in FIG. 8B). A fractured destructible member 812 releases the tether 810 from the engagement member 808. The engagement member 808 may then freely be deployed into tissue. An elastic member 811 may be attached to the engagement member (e.g., at the second end 808s). The elastic member 811 may be attached to another engagement member or medical instrument. The tether 810 may be a string, a flexible extruded material, an elastic member, a flexible braided material, a flexible stamped material, or the like, including as described with respect to elastic members 110, 210, 310, 410, 710, 811, 910, etc.

Figure 9:
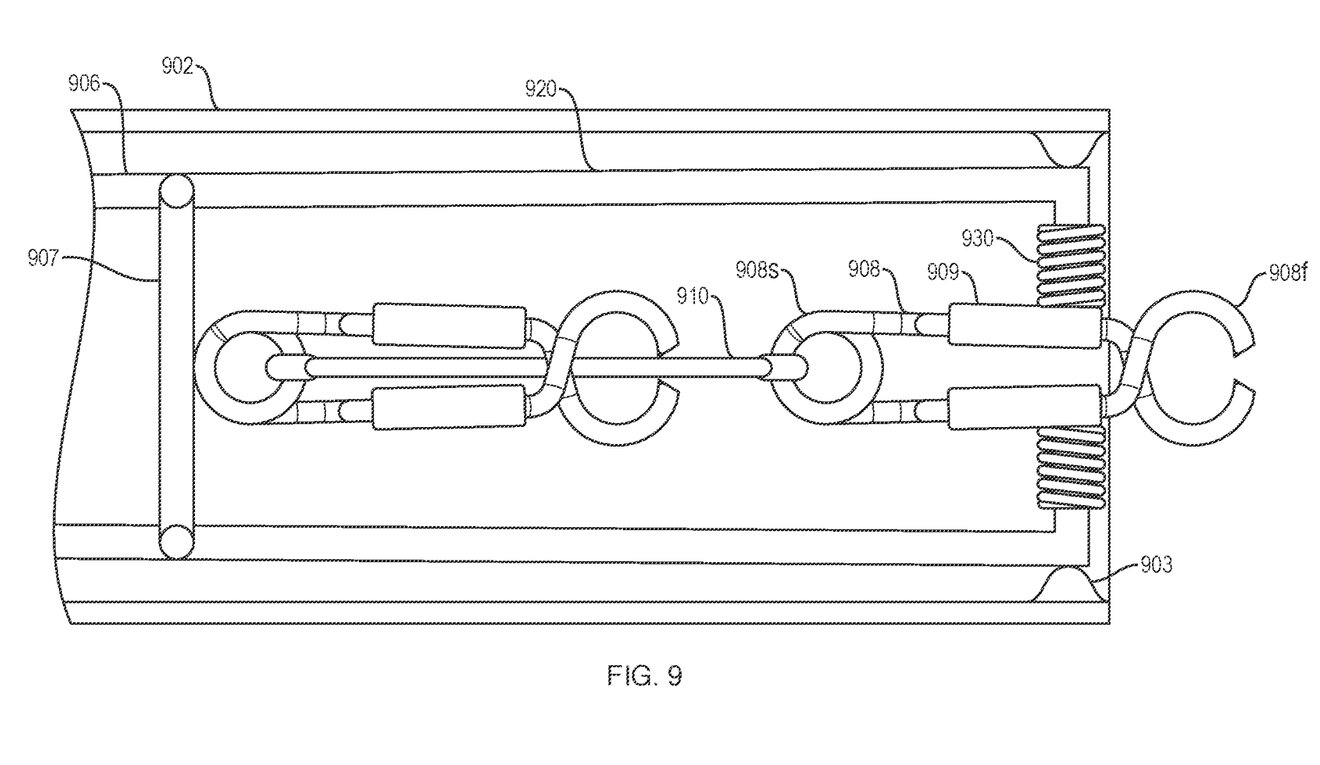
FIG. 9 depicts a tissue retraction system in accordance with an embodiment of the present disclosure.

Referring to FIG. 9, various embodiments of a tissue retractor system, described here or otherwise, within the scope of the present disclosure, may include an engagement member 908 having a first end 908f configured to engage tissue, a second end 908s that may be a spring, and a pair of gripping members 909. An elastic member 910 may connect the second end 908s of the engagement member 908 to another engagement member 908. A pair of springs 930 may each be connected to respective arms 920 of a grasping member 906 at one end of each spring 930 and may each contact a surface of one of the gripping members 909 that faces substantially away from the other gripping member 909 at the other end of each spring 930. The grasping member 906 may grasp the engagement member 908 by compressing the springs 930 against the gripping members. The grasping member 906 and engagement members 908 may be loaded into a catheter 902 with the engagement members 908 facing the same direction (i.e., the first end 908f of each engagement member 908 being distal to the second end 908s). The catheter 902 may have a distal end 903 having a diameter that is narrower than a diameter of the rest of the catheter 902. The grasping member 906 may be advanced distally through the catheter 902 with the engagement member 908. Once the grasping member 906 reaches the narrower distal end 903 of the catheter 902, the distal end 903 may compress the arms 920 towards each other. This compression may actuate the springs 930 and engagement member 908 such that the first end of the engagement member 908f may open for the engagement of tissue. With the first engagement member 908 in position within the body lumen, a second engagement member 908 may then be advanced to a position at the distal end 903 of the catheter 902. After the first engagement member 908 is deployed, the second engagement member 908 may be placed into position within the body lumen in a similar manner as the first engagement member 908. With the first engagement member 908 attached to a target tissue at the first end 908*f* and the elastic member 910 at the second end 908*s*, the grasping member 906 and arms 920 may be retracted proximally such that the grasping member arms 920 are proximal to the distal end 903 of the catheter 902, and the arms with the springs are not compressed by the reduced diameter of the catheter. The catheter 902 and/or grasping member 906 may then be retracted proximally, causing the second engagement member 908 to advance distally and seat itself between the springs 930 because it is attached to elastic member 910. The second engagement member 908 and grasping member 906 and arms 920 with the second engagement member seated between springs 930 may then be advanced distally to the distal end 903 of the catheter 902 into the same position for deployment in the target tissue that the first engagement member 908 is in as illustrated in FIG. 9. Alternatively or additionally, the second engagement member 908 may be advanced to the deployment position between springs 930 by a mechanism 907 on the grasping member 906. The mechanism 907 may urge the second grasping member 908 to the distal end 903 of the catheter 902.

Figures 10A, 10B:
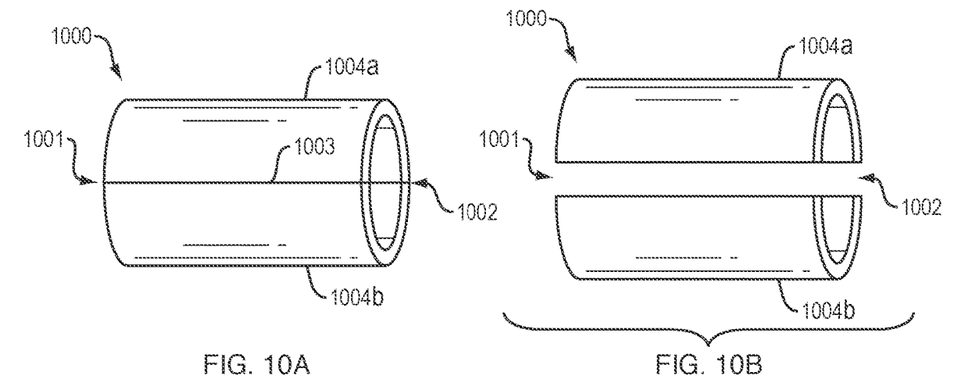
FIGS. 10A through 10F depict casings in accordance with embodiments of the present disclosure.
Figures 10C, 10D:
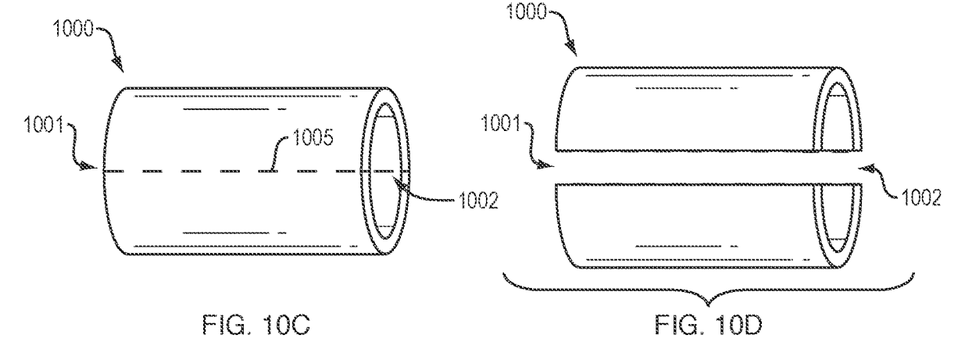
Figure 10E:
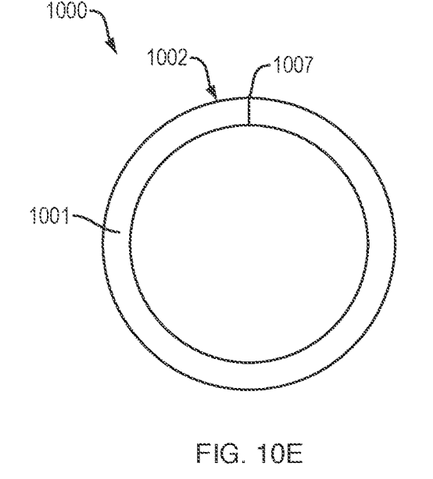
Figure 10F:
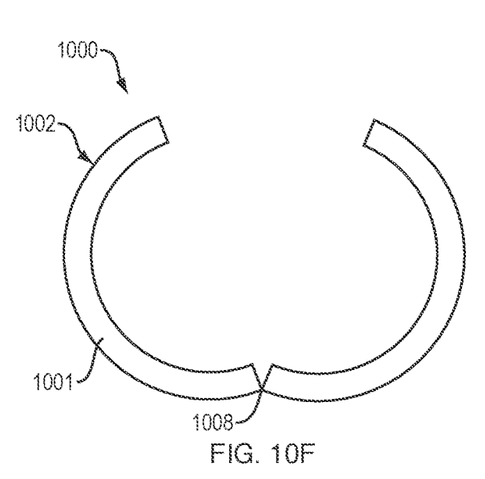

Referring to FIGS. 10A-10F, various embodiments of a tissue retractor system, described here or otherwise, within the scope of the present disclosure, may include a casing 1000 having a first open end 1001, a second end 1002 that may be closed or open, and a body therebetween. The casing 1000 may be a biodegradable material and/or may be small enough for a patient to harmlessly pass the casing naturally 1000. The casing may be disposed about the first end of an engagement member (e.g. the setup of the casing 216 in FIG. 2). The casing 1000 may have a line of separation extending from the first end 1001 to the second end 1002 that may or may not be at least partially or totally perforated. In FIGS. 10A and 10B, a casing 1000 has a line of separation 1003 that allows the casing 1000 to separate into a first piece 1004*a* and a second piece 1004*b*. This separation (i.e., from 10A to 10B) may occur once the casing 1000 is no longer restricted in a catheter and/or working channel and is deployed into a body lumen. In FIGS. 10C and 10D, a casing 1000 may have a perforation line 1005 from the first end 1001 at least substantially up to the second end 1002. The casing 1000 may separate into multiple pieces as shown in FIG. 10D by a force that separates the connected portions along the perforation line 1005. This force may be, for example, an actuation of a first end of an engagement member, the compression force of a grasping member, or the release of the constraint at the catheter or working channel from about the grasping member and casing. In FIGS. 10E and 10F, a casing 1000 may have a line of separation 1007 that does not extend completely through the opposing side of the casing 1000. The casing 1000 may separate along the line of separation 1007 and at least partially fracture at a fracture section 1008.

In various of the above, and other embodiments, a medical professional may setup a system for retracting tissue by back-loading a first working channel of an endoscope with a first grasping member extending out a distal end of the endoscope. A second working channel of the endoscope may be back-loaded with a second grasping member extending out the distal end of an endoscope. A first engagement member having a first end configured to engage tissue and a second end may be back-loaded such that a first grasping member is disposed about the first end of the first engagement member. A second engagement member having a first end configured to engage tissue and a second end may be loaded such that a second grasping member is disposed about the first end of the second engagement member. The first and second grasping members and the first and second engagement members may be disposed within in a cylindrical cap extending from the distal end of the endoscope. A first end of the first and second engagement members may be oriented in a distal direction that is substantially parallel to a longitudinal axis of the endoscope.

In various of the above, and other embodiments, a medical professional may advance a tissue retraction device or system of this disclosure through and/or out of a working channel, catheter, and/or cap during a medical procedure. This may be performed by advancing a grasping member or other medical instrument to push and/or manipulate an engagement member (e.g., in a proximal-to-distal direction). The grasping member may force the tissue retracting device forward and out of the working channel and/or delivery catheter into the body lumen of a patient. The device may be positioned adjacent to the target tissue.

In various of the above, and other embodiments, a medical professional may manipulate a distal end (e.g., first end) of an engagement member toward a target tissue. A grasping member may acquire an engagement member by manipulating the arms of the grasping member around one or more of the gripping members of the engagement member. For example, the grasping member may open and then close its arms around the gripping members of an engagement member, opening the first end of the engagement member for engaging tissue. The grasping jaws may manipulate the location of the engagement member such that the first end of the engagement member is adjacent the target tissue. The grasping member may be actuated to open its arms thereby releasing the engagement member and allowing the first end of the engagement member to engage the target tissue. A second engagement member may be similarly manipulated by the grasping member. The second engagement member may be attached to the first engagement member (e.g., by an elastic member). The second engagement member may be engaged to another section of the target tissue, or to healthy tissue so as to anchor the device and target tissue while a medical professional dissects the target tissue. Should both the first and second engagement members be attached to the target tissue to be dissected, the elastic member may place the target tissue under tension. Once the target tissue is dissected, the elastic member may pull the engagement members towards each other, retracting the target tissue away from the wall of the body lumen.

Devices according to the embodiments described, and in accordance with other embodiments of the present disclosure, alone or in a system or kit or as part of a method or procedure, including with other accessories, may be used in cavities, lumens, tracts, vessels and organs of the body, such as to access, treat or diagnose conditions in the peritoneal, abdominal, bronchial or thoracic cavities, vascular vessels, gastrointestinal or urinary tract, uterus, bladder, lung and liver organs, etc.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. A device configured and adapted to be mounted over a distal end of a tubular device having a lumen extending therethrough, the device comprising:
a cap extending along a longitudinal axis and having a proximal end, a distal end, and a wall with an inner surface defining a lumen through the cap sized to fit over the distal end of the tubular device-to hold the proximal end of the cap on the distal end of the tubular device with the cap lumen communicating with the tubular device lumen; and
an extension member having a proximal end fixedly mounted to the distal end of the cap along the inner surface of the wall of the cap offset from the longitudinal axis of the cap lumen;
wherein the extension member is configured to engage an elongated first tissue engagement member having a first end and a second end a length therebetween, and to hold the first end of the elongated first tissue engagement member in a mounted position with a terminal end of the first end of the elongated first tissue engagement member radially outward of the inner surface of the wall of the cap-and the length of the elongated first tissue engagement member extending radially-inwardly toward the second end of the elongated first tissue engagement member and across the cap lumen to be grasped by a grasping member translated through the tubular device lumen and the cap lumen,
further comprising the first tissue engagement member, wherein the first tissue engagement member has a first end and a second end, the extension member engages the first end of the first tissue engagement member, and the first end of the first tissue engagement member is formed such that the first tissue engagement member may be slid off the extension member by the grasping member as the grasping member is extended distally out of the tubular member.

2. The device of claim 1, wherein the extension member is configured to engage the first end of the first tissue engagement member to hold the first end of the first tissue engagement member at the periphery of the cap with the first tissue engagement member extending from the first end to a second end at an angle of about 90 degrees with respect to the longitudinal axis of the cap lumen.

3. The device of claim 1, wherein the extension member is configured to engage a spring of the first tissue engagement member such that the spring is capable of being disposed about the extension member at a position radially outward from the longitudinal axis of the cap lumen.

4. The device of claim 1, further comprising a clip mounted on the inner surface of the wall of the cap, wherein the clip is configured to engage a second tissue engagement member within the cap lumen.

5. The device of claim 4, wherein the clip is configured to grasp a spring of the second tissue engagement member.

6. The device of claim 4, further comprising an elastic member having a distal end, a proximal end, and a length therebetween, wherein the elastic member is configured to be connected at the distal end and the proximal end thereof to the respective first and second tissue engagement members.

7. The tissue retraction device of claim 4, wherein the clip is configured to orient the second tissue engagement member substantially parallel to the lumen of the cap in a mounted position.

8. The device of claim 1, wherein: the first end of the first tissue engagement member is in the form of a spring; and the spring holds the first end in a tissue engagement configuration.

9. The device of claim 1, wherein the extension member extends along the perimeter of the cap lumen offset from the longitudinal axis of the cap lumen.

10. The device of claim 1, further comprising the first tissue engagement member having a first end and a second end, wherein:
the first tissue engagement member further includes a pair of gripping members disposed between the first end and the second end of the first tissue engagement member; and
the pair of gripping member extends across the cap lumen, with the extension member along the perimeter of the cap lumen offset from the longitudinal axis of the cap lumen, so that the gripping members are accessible across the cap lumen by a grasping member translated through the tubular device lumen and the cap lumen.

11. The device of claim 1, further comprising a clip mounted on an inner surface of the wall of the cap and extending radially inwardly into the cap lumen.

12. The device of claim 1, wherein the extension member is configured such that the first tissue engagement member is slidable off the extension member.

13. The device of claim 1, further comprising a grasping member translatable into the lumen of the cap to grasp a first tissue engagement member engaged with the extension member.

14. The device of claim 13, wherein the grasping member has a pair of arms configured to interface with one or more gripping members of the first tissue engagement member.

15. The device of claim 14, wherein the grasping member arms are configured to engage a pair of gripping members each having a substantially convex surface, the convex surface of one of the pair of gripping members facing away from the other one of the pair of gripping members.

16. The device of claim 1, wherein the first tissue engagement member comprises: a pair of gripping members; a destructible member connected between the gripping members; and a tether having a loop at a distal end that is connected to the destructible member.

17. The device of claim 16, wherein the destructible member is separable when the gripping members are compressed towards each other.

18. The device of claim 13, wherein the extension member is configured such that the first tissue engagement member is slidable off the extension member by distal translation of the grasping member.

19. The device of claim 1, wherein the extension member is a post having a proximal end disposed on a distal end of the wall of the cap.

* * * * *